United States Patent [19]

Hocker et al.

[11] 4,000,152

[45] Dec. 28, 1976

[54] CYCLIC AMINALS OF AROMATIC HETEROCYCLIC COMPOUNDS

[75] Inventors: Jürgen Hocker, Schildgen; Rudolf Merten, Leverkusen, both of Germany

[73] Assignee: Bayer Aktiengesellschaft, Leverkusen, Germany

[22] Filed: Nov. 30, 1973

[21] Appl. No.: 420,495

[30] Foreign Application Priority Data

Dec. 19, 1972 Germany ............ 2262187

[52] U.S. Cl. .......... 260/309.7; 260/308 A; 260/308 D; 260/309; 260/319.1
[51] Int. Cl.² ............ C07D 49/34
[58] Field of Search ............ 260/309.7

[56] References Cited

OTHER PUBLICATIONS

Chem. Ber. 105, 1651–1663 (1972).

*Primary Examiner*—Ethel G. Love
*Attorney, Agent, or Firm*—Burgess, Dinklage & Sprung

[57] ABSTRACT

Cyclic aminals of aromatic heterocyclic compounds useful in the dyestuffs, pharmaceutical and pesticides industries, are prepared by reacting aromatic heterocyclic compounds containing at least one NH-group in a ring with a tetra-aminoethylene.

The cyclic aminals produced have the formula

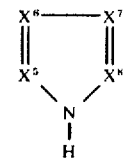

wherein
$X^5$, $X^6$, $X^7$ and $X^8$ are the same or different and are
a. nitrogen; or
b.
$X^5$ is C - $R^3$ and/or
$X^6$ is C - $R^4$ and/or
$X^7$ is C - $R^5$ and/or
$X^8$ is C - $R^6$, wherein
$R^3$, $R^4$, $R^5$ and $R^6$ are the same or different and are selected from the group of hydrogen, optionally substituted aliphatic, aromatic, heterocyclic or araliphatic, and any other radical which does not react with tetra-aminoethylene; or two adjacent radicals together with the carbon atoms substituted thereby can form a fused ring; or
c. the group (Z):

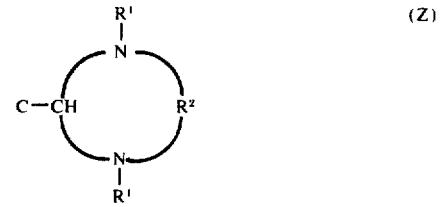

(Z)

wherein
$R^1$ and $R^2$ are as defined in claim 1; and
d. at least one of the radicals $X^5$, $X^6$, $X^7$ and $X^8$ in the group (Z); and
e. when $X^7$ is nitrogen or $X^7$ and $X^8$ together form a fuzed benzene ring, then only $X^5$ and/or $X^6$ can represent the group (Z).

1 Claim, No Drawings

CYCLIC AMINALS OF AROMATIC HETEROCYCLIC COMPOUNDS

This invention relates to new cyclic aminals of aromatic heterocyclic compounds and to a process for the production thereof.

SUMMARY

It has been found that new aminals of aromatic heterocyclic compounds can be obtained by reacting aromatic heterocyclic compounds containing at least one NH-group in a ring with a tetra-aminoethylene corresponding to the general formula (I):

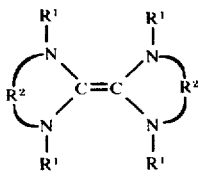

in which
R$^1$ represents an optionally substituted aliphatic, aromatic or heterocyclic radical; and
R$^2$ represents a satured or unsaturated alkylene bridge having up to 3 carbon atoms, optionally substituted by lower alkyl groups, preferably having 1 to 4 carbon atoms, chlorine NO$_2$ or CN, in addition to which a 5- or 6-membered cycloaliphatic ring or a benzene ring may be fused to the alkylene bridge, at temperatures in the range of from −20° to +200° C, preferably at temperatures of from 50° to 180° C and more particularly at temperatures of from 100° to 160° C.

DESCRIPTION

Optionally substituted aliphatic radicals are those having up to 16 carbon atoms, preferably 1 to 8 carbon atoms; these radicals may optionally contain up to 2 double bonds or a triple bond. Aliphatic radicals, of course, also include cycloaliphatic radicals having 5 to 12 carbon atoms and preferably 5 or 6 carbon atoms in the ring system.

Optionally substituted aromatic radicals are those having up to 14, preferably 10, especially 6, carbon atoms in the ring system; in the case of the phenyl radical, it may even be attached through another phenyl radical, optionally by way even then of an oxygen or sulphur atom.

Optionally substituted heterocyclic radicals are those having 5 to 7, preferably 5 or 6, ring members, the heterocyclic ring system optionally containing oxygen, nitrogen or sulphur as hetero atom, in which case this ring system may even be fused with a benzene ring.

Substituents on the aforementioned aliphatic, aromatic or heterocyclic radicals are, for example, aryl (preferably phenyl), CN, NO$_2$, alkylmercapto and alkoxy groups with preferably 1 to 4 carbon atoms, carboxylic ester groups, preferably those with lower aliphatic alcohols, preferably with up to 8 and, more particularly, with up to 4 carbon atoms, and the disubstituted amino group, preferably substituted by lower aliphatic radicals (preferably with 1 to 4 carbon atoms), halogens (preferably fluorine, chlorine and bromine), lower halogen alkyl radicals (preferably having 1 to 4 carbon atoms and preferably with fluorine and/or chlorine) and, in the case of the aromatic and heterocyclic radicals, even lower alkyl groups, preferably with 1 to 4 carbon atoms.

In general, the aromatic heterocyclic compounds used for the process according to the invention correspond to the general formula (II):

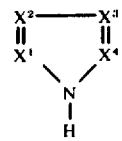

in which
X$^1$, X$^2$, X$^3$ and X$^4$ are the same or different and either
a. represent nitrogen (N), or
b.
X$^1$ represents C - R$^3$ and/or
X$^2$ represents C - R$^4$ and/or
X$^3$ represents C - R$^5$ and/or
X$^4$ represents C - R$^6$,
where
R$^3$, R$^4$, R$^5$ and R$^6$ are the same or different and represent hydrogen; an optionally substituted aliphatic, aromatic, heterocyclic or araliphatic radical or any other radical which does not react with the tetra-aminoethylene used under the reaction conditions; or two adjacent radicals together with the carbon atoms substituted thereby can form a fused ring, at least one of the radicals R$^3$, R$^4$, R$^5$ and R$^6$ having to represent hydrogen, and
c. at least one of the radicals X$^1$, X$^2$, X$^3$ and X$^4$ does not represent nitrogen (N).

The optionally substituted aliphatic, aromatic and heterocyclic radicals R$^3$, R$^4$, R$^5$ and R$^6$ have the same range of meanings as described above with reference to the radical R$^1$, even in regard to their substituents.

In addition, two adjacent radicals (R$^3$ and R$^4$, R$^4$ and R$^5$, R$^5$ and R$^6$), together with the carbon atoms substituted by them, can form a preferably 5-, 6- or 7-membered fused ring which can be carbocyclic or heterocyclic. Heretoatoms for this fused ring include in particular oxygen, nitrogen and sulphur.

Araliphatic radicals (R$^3$ to R$^6$) are those which preferably contain the phenyl radical as aryl radical and which contain from 1 to 6 and preferably from 1 to 3 carbon atoms in the aliphatic portion. Substituents in the aromatic portion of the araliphatic radical include those referred to above in regard to the aromatic radical. The benzyl, phenylethyl, phenylpropyl radical and the 2- and 3-naphthylmethyl, -ethyl- and -propyl radicals are mentioned by way of example.

Examples of radicals which do not react with tetraaminoethylenes under the reaction conditions (radicals R$^3$ to R$^6$) include halogen (preferably fluorine, chlorine and bromine), cyano, nitro, hydroxyl, mercapto, alkylmercapto and alkoxy groups having 1 to 12, preferably 1 to 4 carbon atoms, carboxylic ester and sulphonic acid ester groups, preferably those with lower aliphatic alcohols (preferably having up to 8 and more particularly up to 4 carbon atoms) and the amino group which can preferably be substituted either once or twice by such substituents as, in particular, alkyl-, aryl radicals, preferably lower alkyl radicals with 1 to 8, especially 1 to 4 carbon atoms and the phenyl radical.

The new aminals of aromatic heterocyclic compounds obtainable by the process according to the invention correspond to the general formula (III):

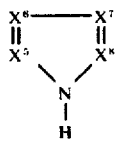
(III)

in which
X⁵, X⁶, X⁷ and X⁸ are the same or different and either
a. represent nitrogen (N) or
b.
X⁵ represents C - R³ and/or
X⁶ represents C - R⁴ and/or
X⁷ represents C - R⁵ and/or
X⁸ represents C - R⁶,
where
R³, R⁴, R⁵ and R⁶ are the same or different and represent hydrogen, an optionally substituted aliphatic, aromatic, heterocyclic or araliphatic radical or any other radical which does not react with tetraaminoethylene, and two adjacent radicals together with the carbon atoms substituted thereby can form a fused ring, or
c. represent the group (Z):

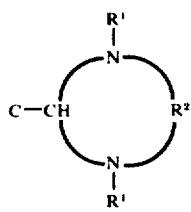
(Z)

in which
R¹ and R² are as defined above, and
d. at least one of the radicals X⁵, X⁶, X⁷ and X⁸ has to represent this group (Z), and
e. when X⁷ represents N or X⁷ and X⁸ together form a fused benzene ring, only X⁵ and/or X⁶ can represent this group (Z).

More particularly, some of the new aminals obtainable by the process according to the invention correspond to the general formula (IV):

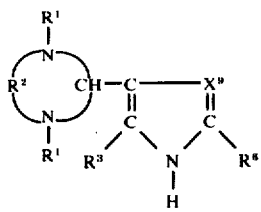
(IV)

in which
X⁹ represents nitrogen (N), the group

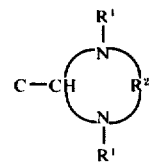

or the group C - R⁵, and R¹, R², R⁴, R⁵ and R⁶ are as defined above.

More particularly, some of the new aminals obtainable by the process according to the invention correspond to the general formula (V):

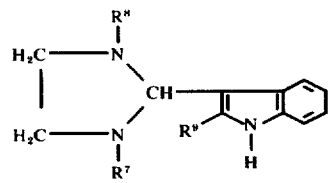
(V)

in which
R⁷ and R⁸ are the same or different and represent an optionally substituted aryl radical; and
R⁹ represents hydrogen, an optionally substituted lower alkyl radical or an optionally substituted aryl radical.

A preferred aryl radical is the phenyl radical, which can be substituted, preferably by halogen, especially chlorine.

Alkyl radicals are, in particular, lower alkyl radicals having up to 4 carbon atoms, preferably the methyl radical.

In addition, some of the new aminals obtainable by the process according to the invention correspond in particular to the following general formula (VI):

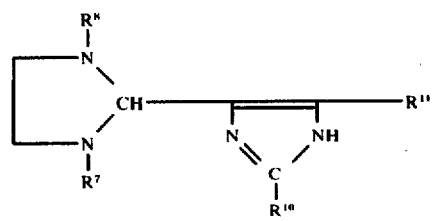
(VI)

in which
R¹⁰ represents hydrogen or a lower alkyl radical having up to 4 carbon atoms;
R¹¹ represents hydrogen or the group:

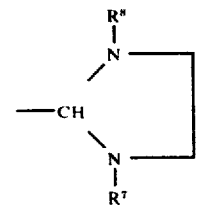

and
R⁷ and R⁸ are as defined above.
The process according to the invention is illustrated with reference to the following reaction scheme:

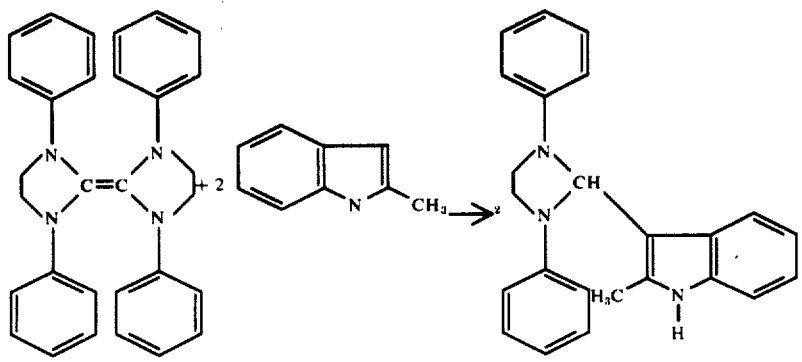

The tetra-aminoethylenes used for the process according to the invention are known or can be obtained by conventional methods. The aromatic heterocyclic compounds used for the process are known from the literature.

The process according to the invention for producing the new aminals of aromatic heterocyclic compounds is generally carried out as follows:

In general, the aromatic heterocyclic compound of formula (II) is employed in the stoichiometrically necessary quantity per mol of the tetra-aminoethylene used. However, it is also possible to use an excess of one of the two starting materials.

In general, the reaction is best carried out in a solvent or diluent, in which case the starting materials can be dissolved or merely suspended. It is, of course, also possible to carry out the reaction in the absence of a solvent or diluent. The reaction is generally carried out by heating the starting materials to the selected reaction temperature, optionally in the presence of the solvent or diluent, and keeping the reaction mixture for a while at the selected reaction temperature.

In general, it is best to carry out the reaction in the absence of atmospheric oxygen, i.e. in an inert-gas atmosphere (for example a noble gas, or carbon dioxide, but preferably nitrogen).

It can be advantageous, especially in cases where readily volatile solvents or diluents are used, to carry out the reaction under pressures higher than normal pressure, for example under a pressure of up to 10, preferably up to 5 atmospheres.

The following represent preferred tetra-aminoethylenes for carrying out the process according to the invention: bis-[1,3-diaryl-imidazolidin-(2)-ylidenes], such as for example bis-[1,3-diphenyl-imidazolidin-(2)-ylidene], bis-[1,3-di-(4-chlorophenyl)-imidazolidin-(2)-ylidene], bis-[1,3-di-(4-methylphenyl)-imidazolidin-(2)-ylidene], bis-[1,3-di-(3-methylphenyl)-imidazolidin-(2)-ylidene], bis-[1,3-di-(2-methylphenyl)-imidazolidin-(2)-ylidene], bis-[1,3-di-(4-methoxyphenyl)-imidazolidin-(2)-ylidene], or bis-[1,3-di-α-(β)-naphthyl-imidazolidin-(2)-ylidene] and substitution products thereof, bis-[1,3-dialkyl imidazolidin-(2)-ylidenes] such as, for example, bis-[1,3-diethyl-imidazolidin-(2)-ylidene].

Such tetra-aminoethylenes are described in Chem. Ber. 96, 1208 (1963), Bull. Chem. Soc. Japan 44, 2171 (1971) and Receuil 88, 289 (1969).

The following are mentioned as examples of aromatic heterocyclic compounds which can be used for the process according to the invention: pyrrole and its substitution products, imidazole and its substitution products, pyrazole and its substitution products, benzpyrazoles and their substitution products, triazoles and their substitution products and tetrazole. The following compounds are mentioned as preferred: pyrrole, 2.methyl-pyrrole, 2-ethyl-pyrrole, 3-ethyl-pyrrole, 2-phenyl-pyrrole, 2,3-dimethyl-pyrrole, 2,5-dimethyl-pyrrole, 3-chloro-pyrrole, indole, 2-methyl-indole, 2-ethyl-indole, 2-phenyl-indole, 2-chloro-indole, imidazole, 2-methyl-imidazole, 2-chloro-imidazole, 2,4-dimethyl-imidazole, 2-phenyl-imidazole, pyrazole, 3-methyl-pyrazole, 3,5-dimethyl-pyrazole, 3-phenyl-pyrazole, benzpyrazole, 1,2,3-triazole, 4-methyl-1,2,3-triazole, 1,2,4-triazole, 3-phenyl-1,2,4-triazole, tetrazole.

In cases where the process is carried out in the presence of solvents, the solvents used should be inert to the reactants. Examples of suitable solvents include aromatic hydrocarbons such as benzene or mesitylene, chlorinated aromatic hydrocarbons such as chlorobenzene or o-dichlorobenzene, and chlorinated aliphatic hydrocarbons such as chloroform or carbon tetrachloride, and also dimethyl-formamide, acetonitrile.

The new aminals of aromatic heterocyclic compounds obtainable by the process according to the invention are valuable intermediate products and can be used for the production of pharmaka, although they can even be directly used as such. As cyclic aminals of heterocyclic compound, they are important starting materials for the synthesis of heterocyclic aldehydes, some of which are extremely difficult to obtain by other methods and which for their part play an important role in the odorant, dyestuffs, pharmaceutical and pesticides industries. These aldehydes may be used instead of aromatic aldehydes in the process of German Pat. No. 860,639. Heterocyclic aldehydes may be used instead of the aromatic aldehydes in the process for preparing triphenyl methane as described in Journal fur paktische Chemie (2) 141, page 311 (1934) or in other dyes as methine dyestuffs (see U.S. Pat. No. 2,374,880).

Hydrolysis of the aminals into the heterocyclic aldehydes can be carried out by conventional methods, both in the presence of alkaline catalysts and also, preferably, in the presence of acid catalysts. In many cases, there is no need to isolate the intermediate aminal.

In the following Examples, temperatures are given in ° C, parts by weight are generally grammes and parts by volume are milliliters.

The abbreviation IR stands for infrared spectrum. The band associated with the NH-group is indicated in the infrared spectrum.

In the elemental analyses, the percent symbols have been left out in accordance with standard practice.

EXAMPLE 1

4.44 parts by weight of bis-[1,3-diphenyl-imidazolidin-(2)-ylidene] and 1.70 parts by weight of 2-methylimidazole in 10 parts by volume of toluene are heated for 60 minutes under nitrogen to boiling point. The clear solution is cooled, followed by filtration under suction, leaving 6.1 parts by weight of toluene-containing 2-(2-methyl-imidazol-4-yl)-1,3-diphenyl-imidazolidine in the form of colourless crystals melting at 210° C (from acetonitrile).

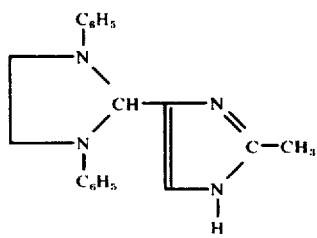

Analysis: Calculated: C, 74.96; H, 6.62; N, 18.42. Found: C, 74.90; H, 6.90; N, 18.50.

EXAMPLE 1a

Hydrolysis of 2-(2-methyl-imidazol-4-yl)-1,3-diphenyl imidazolidine 4.0 parts by weight of 2-(2-methyl-imidazol-4-yl)-1,3 diphenyl imidazolidine are suspended in 7 parts by volume of isopropanol and 4 parts by volume of 10% aqueous hydrochloric acid added. Thereafter water is added and 1.2 parts by weight of 4-formyl-2-methyl imidazole are obtained by by filtering off.

EXAMPLE 2

4.44 parts by weight of bis-[1,3-diphenyl-imidazolidin-(2)-ylidene] and 2.6 parts by weight of 2-methylindole in 15 parts by volume of toluene are heated for 10 hours under nitrogen. to boiling point. 2.2 parts by weight of bis-[1,3-diphenylimidazolidin-(2)-ylidene] are filtered off under suction. After cooling to 0° C, 2.2 parts by weight of 2-(2-methylindol-3-yl)-1,3-diphenylimidazolidine are obtained in the form of colourless crystals melting at 202°-206° C (from toluene).

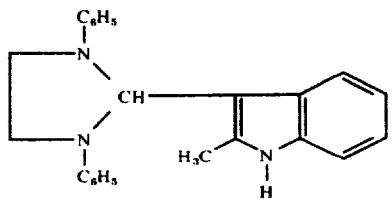

Analysis: Calculated: C, 81.54; H, 6.56; N, 11.89. Found: C, 81.80; H, 6.90; N, 11.80.

EXAMPLE 3

4.44 parts by weight of bis-[1,3-diphenyl-imidazlidin-(2)-ylidene] and 3.86 parts by weight of 2-phenylindole in 20 parts by volume of dimethylformamide are heated under nitrogen for 5 hours to boiling point. A little unreacted bis-[1,3-diphenyl-imidazolidin-(2)-ylidene] is filtered off while still warm, the solvent is removed partly in vacuo and 2-(2-phenylindol-3-yl)-1,3-diphenyl-imidazolidine is obtained in the form of colourless crystals melting at 237°-238° C (from toluene)

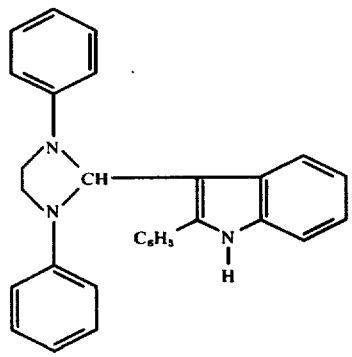

Analysis: Calculated: C, 83.81; H, 6.07; N, 10.12. Found: C, 83.90; H, 6.40; N, 10.10.
IR: 3385 cm$^{-1}$ (NH)

EXAMPLE 3a

Hydrolysis of 2-(2-phenylindol-3-yl)-1,3-diphenyl imidazolidine 4.0 parts by weight of 2-(2-phenylindol-3-yl)-1,3-diphenyl imidazolidine are suspended in 10 parts by volume of isopropanol and 4 parts by volume of 10% aqueous hydrochloric acid added. Thereafter water is added and 1.7 parts by weight of 3-formyl-2-phenyl indole are obtained by filtering off.

EXAMPLE 4

5.82 parts by weight of bis-[1,3-di-(4-chlorophenyl)-imidazolidin-(2)-ylidene] and 1.70 parts by weight of 2-methylimidazole in 20 parts by volume of toluene are heated under nitrogen for 90 minutes to boiling point. The solution is cooled and filtered under suction, leaving 7.1 parts by weight of 2-(2-methylimidazol-4-yl)-1,3-di-(4-chlorophenyl)-imidazolidine in the form of colourless crystals melting at 218°-220° C (from acetonitrile)

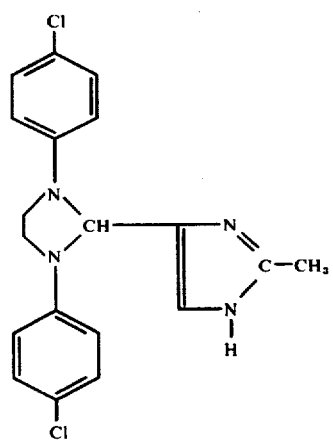

Calculated: C, 61.13; H, 4.85; N, 15.01. Found: C, 60.8; H, 4.8; N, 15.1.

EXAMPLE 5

4.44 parts by weight of bis-[1,3-diphenyl-imidazolidin-(2)-ylidene] and 0.68 parts by weight of imidazole in 20 parts by volume of dimethylformamide are heated under nitrogen for 90 minutes to boiling point. The solvent is removed partly in vacuo, leaving 3.0 parts by weight of 4,5-bis-[1,3-diphenyl-imidazolidin-2-yl]-imidazole in the form of colourless crystals melting at 215° C (toluene/dimethylformamide).

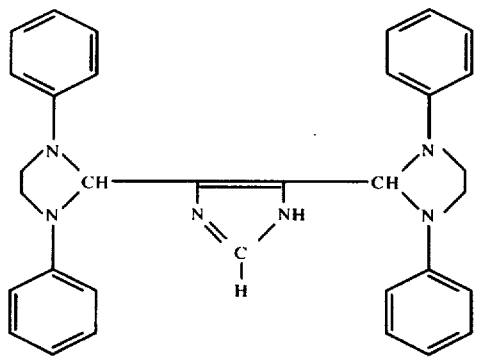

Analysis: Calculated: C, 77.36; H, 6.23; N, 16.40. Found: C, 77.30; H, 5.90; N, 16.40.

IR: 3300 cm$^{-1}$ (wide, NH)

EXAMPLE 6

4.44 parts by weight of bis-[1,3-diphenyl-imidazolidin-(2)-ylidene] and 2.34 parts by weight of indole in 20 parts by volume of toluene are heated under nitrogen for 2 hours to boiling point. The solution is cooled to room temperature, 1.0 part by weight of bis-[1,3-diphenyl-imidazolidin-(2)-ylidene] is filtered off under suction and the solvent is removed partly in vacuo, leaving 4.7 parts by weight of 2-(indol-3-yl)-1,3-diphenyl-imidazolidine in the form of colourless crystals melting at 109°–116° C (from toluene).

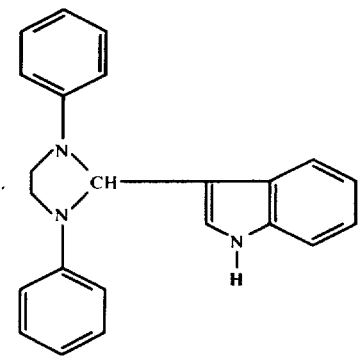

Analysis: Calculated: C, 81.38; H, 6.24; N, 12.38. Found: C, 81.40; H, 6.30; N, 11.40.

IR: 3360 cm$^{-1}$ (NH)

What is claimed is:
1. Compound corresponding to the general formula (V):

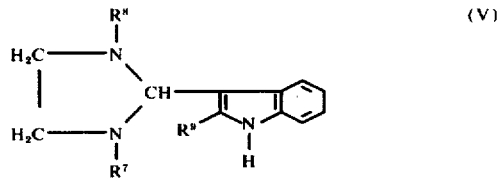

wherein
$R^7$ and $R^8$ are each independently an unsubstituted or halogen substituted phenyl radical; and
$R^9$ is hydrogen, lower alkyl or an unsubstituted or halogen substituted phenyl radical.

* * * * *